United States Patent [19]

Mahood

[11] Patent Number: 5,500,467
[45] Date of Patent: Mar. 19, 1996

[54] POLYOLEFIN FIBER AND FILM RESISTANT TO GAS FADE

[75] Inventor: James A. Mahood, Morgantown, W. Va.

[73] Assignee: General Electric Company, Pittsfield, Mass.

[21] Appl. No.: 360,495

[22] Filed: Dec. 21, 1994

Related U.S. Application Data

[63] Continuation-in-part of Ser. No. 307,545, Sep. 16, 1994, Pat. No. 5,424,348, which is a continuation of Ser. No. 96,530, Jul. 22, 1993, abandoned.

[51] Int. Cl.$^6$ .................................................. C08K 5/527
[52] U.S. Cl. ..................... 524/100; 524/102; 524/103; 524/117; 524/291; 524/350
[58] Field of Search ............................. 524/117, 350, 524/291, 102, 100, 103

[56] References Cited

U.S. PATENT DOCUMENTS

| | | |
|---|---|---|
| 3,039,993 | 6/1962 | Friedman . |
| 3,056,823 | 10/1962 | Hechenbleikner et al. . |
| 3,264,247 | 8/1966 | Friedman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall . |
| 3,509,091 | 4/1970 | Cleveland et al. . |
| 3,558,554 | 1/1971 | Kuriyama et al. . |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Guttag . |
| 4,086,304 | 4/1978 | Hutton et al. . |
| 4,185,004 | 1/1980 | Mathis . |
| 4,196,117 | 4/1980 | Spivack . |
| 4,318,845 | 3/1982 | Spivack et al. . |
| 4,405,739 | 9/1983 | Kinson . |
| 4,529,533 | 7/1985 | Chasar . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,882,374 | 11/1989 | Wang et al. . |
| 4,929,653 | 5/1990 | Kletecka et al. . |
| 4,956,406 | 9/1990 | Myers et al. . |
| 4,957,954 | 9/1990 | Iizuka et al. . |

FOREIGN PATENT DOCUMENTS

| | | |
|---|---|---|
| 184191 | 3/1985 | European Pat. Off. . |
| 2944254 | 5/1980 | Germany . |
| 2087399 | 5/1982 | United Kingdom . |

OTHER PUBLICATIONS

*Phosphorus and Sulfer*, 1983 vol. 15, pp. 9–13.

Primary Examiner—Veronica P. Hoke

[57] ABSTRACT

A polyolefin composition is provided which is resistant to gas fading upon exposure to atmospheric pollutants. The compositions containing a stabilizing amount of a phosphite of the formula $$H_3C-CH_2-CH_2-CH_2 \diagdown \phantom{x} \diagup CH_2-O \diagdown \phantom{xxx}$$

wherein $Y^1$ is an alkyl, preferably t-butyl, and $Y^2$ is t-butyl or sec-butyl. Fibers and films made from the composition exhibit improved fade resistance compared to fibers and films made from polyolefins stabilized with various other commercially available phosphite. The compositions also contain an additive selected from hindered phenolic antioxidants and hindered amine light stabilizers.

13 Claims, No Drawings

POLYOLEFIN FIBER AND FILM RESISTANT TO GAS FADE

This is a continuation-in-part of application Ser. No. 08/307,545, filed on Sep. 16, 1994, U.S. Pat. No. 5,424,348.

BACKGROUND OF THE INVENTION

1. Field of the Invention

The present invention relates to polyolefin fibers and films, and more particularly relates to polyolefin fibers and films containing a phosphite stabilizer.

2. Description of the Related Art

Polyolefin fibers and films, such as polypropylene fibers and films, containing a hindered phenolic and hindered amine light stabilizer can exhibit undesirable color formation (yellowing) upon extended exposure to atmospheric pollutants such as nitrogen oxides, see Kletecka et al., U.S. Pat. No. 4,929,653, issued May 29, 1990, which is incorporated herein by reference. Fabric and material made with polyolefin fiber or polyolefin film is susceptible to yellowing upon exposure to these gases, which can be generated through vehicular exhausts and can be present under warehouse storage conditions. It is believed that the presence of hindered sine light stabilizers and hindered phenolic antioxidants in the fiber and film contributes to this undesirable gas fading characteristic.

Accordingly, there is a need to provide a phosphite stabilized polyolefin composition and fibers films made therefrom which exhibit increased resistance to gas fading.

SUMMARY OF THE INVENTION

Polyolefin fibers and films resistant to gas fading are provided, as well as a method for imparting gas fade resistance to polyolefin fibers. The fibers and films are made from a polyolefin composition containing a phosphite of the formula:

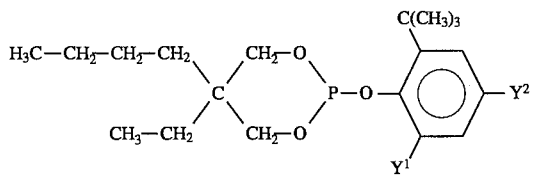

wherein $Y^1$ and $Y^2$ are as defined below. The polyolefin is preferably polypropylene. The composition further contains a hindered amine light stabilizer and/or a hindered phenolic antioxidant.

DETAILED DESCRIPTION OF THE INVENTION

Various considerations relating to the "gas fade resistance" of fabrics are discussed in "Why Do White Fabrics and Garments Turn Yellow During Storage in Polyethylene Bags and Wrappings?" by Kenneth C. Smeltz, Textile Chemist and Colorist, Vol. 15, No. 4, April 1983, pp. 17–21. Specific considerations relating to the use of pigments in PP fibers are discussed in "Influence of Pigments on the Degradation of Polypropylene Fibers on Exposure to Light and Weather" by Steinlin, F. and Saar, W., Melliand Textilberichte, Nov. 1980, pp. 1465–70. A detailed overall analysis of various aspects of yellowing is discussed in a compendium of articles titled "Update on Yellowing" Textile Progress, Vol. 15, No. 4 (published by Textile Institute 1987).

In a particular embodiment, this invention provides fibers and films made from pigmented propylene polymer (PP) stabilized against degradation by uv-light, which fibers are subjected to exposure to nitrogen oxides under conditions which cause the fibers to yellow. Preferably incorporated in the polymer composition, and preferably uniformly distributed therein, in addition to the pigment and a lubricant or processing aid, is a small amount of a hindered phenolic, from about 20 ppm to about 2.0% by weight (based on the weight of all the polymer from which the article is formed), and a neoalkyl phosphite at a level of from 50 ppm to 2000 ppm by weight (based on the total weight of polymer in the composition from which the fiber or film is formed).

The polymer is preferably a polyolefin polymer. The propylene polymer is typically polyethylene or polypropylene, but may be a random or block copolymer, such as a block copolymer of propylene and a monoolefinically unsaturated monomer X (P-co-X) with up to about 10% by wt of X wherein X represents vinyl acetate, ethylene or a lower $C_1$-$C_4$ alkyl acrylate or methacrylate. Blends of such propylene polymers with a minor amount of another polymer such as polyethylene are also included within the scope of this invention. For convenience, homopolymer PP and copolymer P-co-X are together referred to herein as "propylene polymer" PP. The PP has a number average mol wt Mn in the range from about 10,000 to about 500,000, preferably bout 30,000 to about 300,000 with a melt flow index from 0.1 to 30 g/10 min when measured according to ASTM D-1238.

More important, PP fibers may be provided with a surface "finish" comprising an alkoxylated lubricant and a phosphate ester, and optionally, additives such as bactericides and antistats, which are effective because they tend to concentrate on the surface of the fibers. A description of ethoxylated lubricants is given in Kirk-Othmer, Encyclopedia of Chemical Technology, 2nd Edition 19,531–554 (1969), and of the polyethylene glycols, etc. in 10,654–659, id. Commonly favored finishes are of the lubricant type selected from ethoxylated sorbitol esters, fatty acid, fatty acid amides, fatty acid esters, random copolymers of the monobutyl ether of poly(oxyethyleneoxy 1,2-propylene), the methyl ether of poly(oxyethyleneoxy 1,2-propylene) laurate, etc. to which is added a phosphate type antistatic material such as hydrocarbyl phosphate ester, ethoxylated hydrocarbyl phosphate esters, partially hydrolyzed hydrocarbyl phosphate esters, or their salts. Commercially available finishes are Napcostar, available from Diamond Shamrock Corp., and particularly finishes such as those described in U.S. Pat. No. 4,185,004 or European Patent Publication No. 0 184 191 filed Mar. 12, 1985, relevant portions of the disclosures of which are incorporated by reference thereto as if fully set forth herein. Test samples of pigmented fiber were prepared with a Napcostar finish, and a finish, designated "P-7" prepared as generally disclosed in the foregoing disclosures.

Since a predominant concern is the unwanted development of yellow color, the neoalkyl phosphite-containing stabilizer is particularly beneficial in fibers where no pigment has been added to the normally water white PP. However, if the fibers are to be pigmented with an opaque white pigment, or a pastel color is desired, for example, with pink and blue azo dyes, the resistance to gas fade will be improved by the neoalkyl phosphite-containing stabilizer. Blue may also be obtained with a phthalocyanine pigment, but in all cases, the amount of pigment added is sufficient to provide the desired color, but insufficient adversely to affect the uv-stabilization provided by the neoalkyl phosphite-containing stabilizer.

The neoalkyl phosphite-containing stabilizer may readily be incorporated into the PP by any conventional technique at a convenient stage prior to the manufacture of the fiber from the PP. For example, the stabilizer may be mixed with the PP in the melt, which is then spun into fibers in the range from about 8 denier to about 30 denier, most preferably about 10–15 denier.

The phosphite is a compound of the formula:

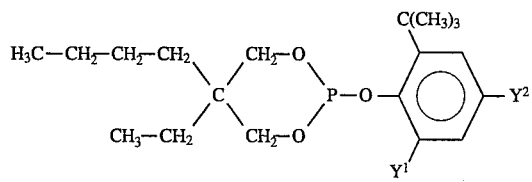

wherein $Y^1$ and $Y^2$ are defined below.

The phosphite may be made by the reaction of 2-ethyl-2-butyl-1,3-propane diol with $PCl_3$ in the absence of a catalyst, HCl acceptor and solvent to produce an intermediate product of the formula:

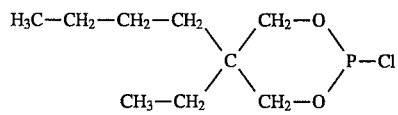

followed by the reaction with a hydroxyaryl compound of the formula:

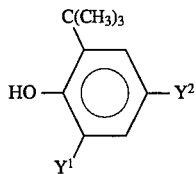

wherein $Y^1$ and $Y^2$ are as defined below. Suitable reaction methods are set out in Great Britain Patent 2087399A, U.S. Patent Spivak et al. 4318845 issued 1982, and Article in Phosphourous & Sulfur Journal by J. D. Spivak et al. 1983, vol. 15, pp. 9–13, all of which are incorporated herein by reference.

The reaction between the diol and $PCl_3$ may be conducted in known manner, as by mixing the reactants together at room temperature, or preferably, by cooling the $PCl_3$ to a temperature between 5–15 degrees centigrade prior to addition of diol to the reactor. An excess of either reactant may be employed although it is preferred to operate with substantially stoichiometric amounts of the diol and $PCl_3$. The reaction temperature is preferably maintained between 5–15 degrees centigrade. This temperature may be readily controlled by regulating the rate of diol addition. The esterification reaction is quite exothermic in the absence of a solvent, but a temperature moderating effect is produced by the cooling effect of vigorous HCl evolution. Hence, by effective control of diol addition, the reaction may be made self-regulating in the temperature range between 5–15 degrees centigrade.

After the reaction has gone to completion, the bulk of the by-product HCl may optionally be removed by gently raising the temperature of the product to about 50 degrees centigrade and applying a vacuum.

The reaction between the intermediate product of the reaction discussed in the preceding paragraph and hydroxyaryl compound may be conducted in the same reaction vessel that was employed to produce the crude intermediate by merely introducing the hydroxyaryl compound into the reactor.

The reaction between the hydroxyaryl compound and the intermediate product in some instances may be carried out at a temperature between 35 to 100 degrees centigrade and preferably between about 45 to about 80 degrees centigrade. The pressure of the reaction system is maintained between about 50 millimeters mercury absolute to atmospheric pressure. The reaction reaches substantial completion in from 1 to about 8 hours and for practical purposes it is preferably operated under temperature and pressure conditions which will afford the maximum amount of product within 3 to about 5 hours. Although a stoichiometric excess of either reactant may be employed, it is preferred to operate with substantially stoichiometric quantities.

The hydroxyaryl compound may be any compound of the formula:

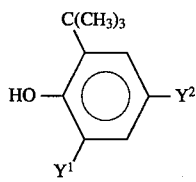

in which $Y^1$ is selected from the group consisting of alkyl groups preferably having from 1 to 8 carbon atoms, more preferably methyl or t-butyl. The reaction can be completed in the presence of a base such as an amine acceptor. Since $Y^1$ is an alkyl group, an amine acceptor should be added to help drive this reaction. If $Y^1$ is a tert-alkyl group, such as t-butyl, then a stociometeric amount of amine acceptor should be present. $Y^2$ is selected from sec-butyl and t-butyl groups. If $Y^2$ is a t-butyl group then the phosphite is a solid at room temperature. Preferably $Y^2$ is sec-butyl so that the phosphite is a liquid at room temperature.

After completion or near completion of the reaction, HCl generated during the process may readily be substantially removed by evacuating the reactor vessel. No special precautions need to be taken to remove all the HCl present, as by addition of HCl acceptor or via controlled neutralization of the acidity. The product may then be recovered by distillation, or crystallization.

The phosphites have $Y^1$ as an alkyl group such as methyl or t-butyl in order to inhibit ultraviolet light yellowing of the phosphite. If $Y^1$ is hydrogen the phosphite will have sensitivity to UV yellowing. The preferred phosphite has a phenolic degradation product boiling point of greater than 250° C., more preferably greater than 260° C. so that the volatility of the degradation product during processing of the stabilized polymer, such as polyolefins such as polypropylene which processes at 240° C. and above, is minimized. The problem of excessive volatiles can be minimized by employing an 2,4-di-t-butyl-6-alkyl phenyl group because such groups have corresponding 2,4-di-t-butyl-6-alkyl phenol degradation products which have a boiling point of greater than 260° C.

The stabilized polymer composition which includes an effective amount of the phosphite described above. An amount of the phosphite of the invention is considered to be an "effective amount" when the polymer composition containing the phosphite of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more.

In a broader sense, polyolefins may be defined as follows:

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene; as well as mixtures of such copolymers and their mixtures with polymers mentioned above, for example polypropylene/ethylene propylene-copolymers, LDPE/EVA, LDPE/EAA, LLDPE/EVA and LLDPE/EAA.

The resulting stabilized polymer compositions of the invention may optionally also contain various conventional additives, such as the following:

1. Antioxidants (including hindered phenols)

1.1 Alkylated monophenols, for example: 2,6 -di-tertbutyl-4-methylphenol, 2 -tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl - 4-methylphenol, 2-(alpha-methylcyclohexyl) -4,6 dimethylphenol, 2,6 -di-octadecyl-4-methylphenol, 2,4,6,-tricyclohexyphenol, 2,6-di-tert-butyl-4 -methoxymethylphenol.

1.2 Alkylated hydroquinones, for example, 2,6-di-tertbutyl-4-methoxyphenol, 2,5 -di-tert-butyl-hydroquinone, 2,5-di-tert-amyl-hydroquinone, 2,6-diphenyl- 4octadecyloxyphenol.

1.3 Hydroxylated thiodiphenyl ethers, for example, 2,2'-thio-bis-(6-tert-butyl-4-methylphenol) 2,2'-thio-bis-(4-octylphenol), 4,4'thio-bis-(6-tert-butyl-3-methylphenol), 4,4' -thio-bis -(6-tert -butyl-2-methylphenol).

1.4 Alkylidene-bisphenols, for example, 2,2'-methylenebis-(6-tert-butyl-4-methylphenol), 2,2'-methylene -bis -(6-tert -butyl-4-ethylphenol), 2,2'-methylene -bis -(4-methyl-6-(alpha-methylcyclohexyl (phenol), 2,2'-methylene-bis-(4 -methyl-6-cyclohexylphenol), 2,2' -methylene-bis-(6-nonyl-4-methylphenol), 2,2'-methylene-bis-(6 -nonyl-4-methylphenol), 2,2'-methylene-bis-(6 -(alpha-methylbenzyl) -4-nonylphenol), 2,2'-methylene -bis -(6-(alpha, alpha-dimethylbenzyl) -4 -nonyl-phenol). 2,2'-methylene-bis-(4,6-di-tert-butylphenol) 2,2'-ethylidene-bis-(6 -tert-butyl-4-isobutylphenol), 4,4'-methylene-bis-(2,6 -di-tert-butylphenol), 4,4'-methylene-bis-(6 -tert-butyl-2-methylphenol), 1,1-bis-(5-tert-butyl-4 -hydroxy-2-methylphenol)butane. 2,6-di-(3 -tert-butyl-5-methyl-2-hydroxybenzyl)-4-methylphenol, 1,1,3-tris-(5-tert-butyl-4-hydroxy-2 -methylphenyl)butane, 1,1-bis-(5-tert-butyl-4 -hydroxy-2-methylphenyl)-3-dodecyl-mercaptobutane, ethyleneglycol-bis-(3,3,-bis-(3'-tert-butyl-4' -hydroxyphenyl)-butyrate)-di-(3-tert-butyl-4 -hydroxy-5-methylphenyl)-dicyclopentadiene, di-(2-( 3'-tert-butyl-2'hydroxy-5'methyl-benzyl)-6 -tert-butyl-4-methylphenyl)terephthalate.

1.5 Benzyl compounds, for example, 1,3,5 -tris-(3,5-ditert-butyl-4-hydroxybenzyl)-2,4,6-trimethylbenzene, bis-(3, 5-di-tert-butyl-4-hydroxybenzyl)sulfide, isooctyl 3,5 -di-tert-butyl-4-hydroxybenzyl-mercapto-acetate, bis-(4 -tert-butyl-3-hydroxy-2,6-dimethylbenzyl)dithiolterephthalate. 1,3,5-tris-(3,5-di-tert-butyl-4-hydroxybenzyl)isocyanurate. 1,3,5-tris-(4 -tert-butyl-3-hydroxy-2,6-dimethylbenzyl)isocyanurate, dioctadecyl 3,5-di-tert-butyl-4-hydroxybenzylphosphonate, calcium salt of monoethyl 3,5 -di-tert-butyl-4-hydroxybenzylphosphonate, 1,3,5 -tris-(3,5-dicyclohexyl-4-hydroxybenzyl)isocyanurate.

1.6 Acylaminophenols, for example, 4 -hydroxy-lauric acid anilide, 4-hydroxy-stearic acid amilide, 2,4-bis-octylmercapto-6-(3,5 -tert-butyl-4-hydroxyanilino)-s-triazine, octyl-N-(3,5 -di-tert-butyl-4-hydroxyphenyl)-carbamate.

1.7 Esters of beta-(3,5-di-tert-butyl-4 -hydroxyphenol)-propionic acid with monohydric or polyhydric alcohols, for example, methanol, diethyleneglycol, octadecanol, triethyleneglycol, 1,6-hexanediol, penta-erythritol, neopentylglycol, tris-hydroxyethyl isocyanurate, thiodiethyleneglycol, di-hydroxyethyl oxalic acid diamide.

1.8 Esters of beta-(5-tert-butyl-4 -hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy- 3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4 -hydroxyphenol)-propionic acid for example, N,N' -di-(3,5-di-tert-butyl-4 -hydroxyphenylpropionyl)-hexamethylen-diamine, N,N'-di-(3,5-di-tert-butyl- 4-hydroxyphenylpropionyl)trimethylenediamine, N,N'-di-(3,5-di-tert-butyl-4 -hydroxyphenylpropionyl)-hydrazine.

2. UV absorbers and light stabilizers.

2.1 2-(2'-hydroxyphenyl)-benzotriazoles, for example, the 5'methyl-,3'5'-di-tert-butyl- 5'-tert-butyl-,5'(1,1,3,3-tetramethylbutyl)-,5 -chloro-3',5'-di-tert-butyl-,5-chloro-3' -tert-butyl-5'methyl-,3'sec-butyl-5'tert-butyl-,4'-octoxy, 3',5'-ditert-amyl-3',5'-bis-(alpha, alpha-dimethylbenzyl)-derivatives.

2.2 2-Hydroxy-benzophenones, for example, the 4-hydroxy-4-methoxy-,4-octoxy,4-decloxy-,4 -dodecyloxy-,4-benzyloxy,4,2',4'-trihydroxy-and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-( 4-tert-butylbenzoyl)-resorcinol, benzoylresorcinol, 2,4-di-tert-butylphenyl-3,5 -di-tert-butyl-4-hydroxybenzoate and hexadecyl-3,5-di-tert-butyl-4-hydroxybenzoate.

2.4 Acrylates, for example, alpha-cyanobeta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2 -methylindoline.

2.5 Nickel compounds, for example, nickel complexes of 2,2'-thio-bis(4-(1,1,1,3 -tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6 -tetramethyl-4-hydroxy-piperidine and succinic acid, condensation product of N,N'-(2,2,6,6-tetramethylpiperidyl)-hexamethylendiamine and 4 -tert-octylamino-2,6-dichloro-1,3,5-s-triazine, tris-(2,2,6,6-tetramethylpiperidyl)-nitrilotriacetate, tetrakis-(2,2,6,6-tetramethyl- 4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl- 4-(3,5-di-tert-butyl-4-hydroxy hydrocinnamoyloxy)-piperdine; and N-(1-hydroxy-2,2,6,6-tetramethyl-piperidin-4-yl)-epsiloncaprolactam.

2.7 Oxalic acid diamides, for examples, 4,4'-dioctyloxyoxanilide, 2,2' -di-octyloxy-5',5'-di-tert-butyloxanilide, 2,2' -di-dodecyloxy-5',5'di-tert-butyl-oxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy- 2'ethyl-5,4-di-tert-butyloxanilide and mixtures of ortho-and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bissalicyloylhydrazine, N,N'-bis-(3,5 -di-tert-butyl-4-hydrophenylpropionyl)-hydrazine, salicyloylamino-1, 2,4-triazole, bis-benzylidenoxalic acid dihydrazide.

4. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl)4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmirate, antimony pyrocatecholate or zinc pyrocatecholate.

8. Nucleating agents, for example, 4-tert butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate; ethyl-3-(N,N-dibenzylaminoxy)propanoate; 1,6-hexamethylene-bis (3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3 -(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, epoxidized vegetable oils, such as expoxidized soybean oils, lubricants, emulsifiers, pigments, hydroxylamines such as $R_2NOH$ wherein R is a $C_1$ to $C_{30}$ alkyl group such as propyl or stearyl, optical brighteners, flameproofing agents, anti-static agents, blowing agents and thiosynergists such as dilaurythiodipropionate or distearylthiodipropionate. Optionally, the polyolefin compositions, and fibers and films made therefrom, may be free of one or more of the above additives.

The additives such as hindered phenolic antioxidants and hindered amine light stabilizer may be present at levels of from 0.01 to 2 percent by weight based on the total weight of the polymer composition (or film or fiber), more preferably from 0.02 to 1 percent by weight thereof, and most preferably from 0.04 to 0.06 percent by weight thereof.

EXAMPLES

TABLE 1

| Ex | Phos | YI change (16 hours) |
|----|------|----------------------|
| A | none | 4.94 |
| 1 | Phos 1 | –0.16 |
| B | Phos B | 1.25 |
| C | Phos C | 1.53 |
| D | Phos D | 3.25 |
| E | Phos E | 3.82 |

TABLE 2

| Ex | Phos | YI change (16 hours) |
|----|------|----------------------|
| F | none | 3.12 |
| 2 | Phos 1 | 0.06 |
| G | Phos B | 1.58 |
| H | Phos C | 1.55 |
| I | Phos D | 2.09 |
| J | Phos E | 1.87 |

The compositions of Examples A–E and 1 contained 1,000,000 parts by weight polypropylene (commercially available as Profax 6501), 500 ppm of a hindered phenolic (commercially available as Irganox -1010), 500 ppm (parts by weight per million of polypropylene) of calcium stearate, and 1000 ppm of the listed Phosphite (Phos). The compositions of Examples F–J and 2 contained 1,000,000 parts by weight polypropylene (commercially available as Profax 6501), 250 ppm of a hindered phenolic (commercially available as Irganox -1010), 500 ppm (parts by weight per million of polypropylene) of calcium stearate, and 500 ppm of the listed Phosphite (Phos).

Phos 1 is of the formula

Phos B is Tetrakis(2,4-di-tert-butylphenyl) 4,4'bipheny- lylenediphosphonite.

Phos C is trisnonylphenyl phosphite.

Phos D is 2,2'Ethylidenebis(4,6-di-tert-butylphenyl)fluo- rophosphite.

Phos E is Tris(2,4-di-tert-butylphenyl) phosphite.

Tables 1 and 2 contain yellowness index changes after exposure of the polypropylene compositions to gases containing nitrous oxide.

What is claimed is:

1. A polyolefin fiber comprising a polyolefin and in an amount effective to provide thermal and UV light stabilization, a stabilizer composition comprising:

(a) a phosphite of the formula:

wherein $Y^1$ is an alkyl, and $Y^2$ is selected from t-butyl and sec-butyl, (b) an additive selected from the group consisting of a hindered phenolic antioxidant and a hindered amine light stabilizer.

2. The fiber of claim 1 wherein $Y^1$ is methyl.

3. The fiber of claim 1 wherein $Y^1$ is t-butyl.

4. The fiber of claim 1 wherein said fiber is made from a polypropylene composition comprising from 0.01 to 1.0 percent by weight of said phosphite.

5. The fiber of claim 1 wherein $Y^2$ is t-butyl.

6. The fiber of claim 1 wherein said fiber is a polyethylene fiber.

7. The fiber of claim 1 wherein said fiber comprises a pigment.

8. A method for imparting gas fade resistance to polyolefin fiber, comprising a polyolefin and in an amount effective to provide thermal and UV light stabilization, a stabilizer composition comprising:

(a) mixing into a melt of polypropylene resin,
        (i) a phosphite of the formula:

wherein $Y^1$ is an alkyl, and $Y^2$ is selected from t-butyl and sec-butyl, and
        (ii) a hindered phenolic antioxidant.

(b) spinning said melt into fibers.

9. The method of claim 1 wherein said fibers are free of hindered amines.

10. The method of claim 1 wherein $Y^1$ is methyl.

11. The method of claim 1 wherein $Y^1$ and $Y^2$ are each t-butyl.

12. The method of claim 1 wherein said fiber is a polypropylene fiber.

13. A polyolefin film comprising a polyolefin and in an amount effective to provide thermal and UV light stabilization, a stabilizer composition comprising:

(a) a phosphite of the formula:

wherein $Y^1$ is an alkyl, and $Y^2$ is selected from t-butyl and sec-butyl, (b) an additive selected from the group consisting of a hindered phenolic antioxidant and a hindered amine light stabilizer.

* * * * *